United States Patent [19]

Chatanier et al.

[11] 4,446,424

[45] May 1, 1984

[54] SURFACE RESISTIVIMETER

[75] Inventors: Michel J. Chatanier, Saint Maur; Michel J. Portat, Villebon sur Yvette; Alain E. Bruere, Chevilly-Larue, all of France

[73] Assignee: Office National d'Etudes et de Recherches Aerospatiales, Chatillon, France

[21] Appl. No.: 302,618

[22] Filed: Sep. 15, 1981

[30] Foreign Application Priority Data

Oct. 17, 1980 [FR] France ............................... 80 22329

[51] Int. Cl.$^3$ ...................... G01R 27/02; G01R 27/26
[52] U.S. Cl. ..................................... 324/62; 324/65 P
[58] Field of Search ............... 324/61 R, 62, 64, 65 P, 324/61 P

[56] References Cited

U.S. PATENT DOCUMENTS

| 4,075,557 | 2/1978 | Jurca | 324/62 |
| 4,218,650 | 8/1980 | Matzen | 324/62 |
| 4,335,350 | 6/1982 | Chen | 324/62 X |

FOREIGN PATENT DOCUMENTS 1333449  9/1962  France .

OTHER PUBLICATIONS

Batt: "Surface Resistivity and Power Measurement"-Colloquium on the Measurement of Power at Higher Microwave Freqs.-London-UK-Jan. 1979.
Phillips: "Versatile Four Probe AC Conductivity Measurement System" Rev. Sci. Instruments-Feb. 1979-pp. 263-265.

Primary Examiner—Stanley T. Krawczewicz
Assistant Examiner—Jose M. Solis
Attorney, Agent, or Firm—Lowe, King, Price & Becker

[57] ABSTRACT

Resistivimeter device for measuring the surface resistance of a structure coated with an inner resistive layer and an outer insulating superficial layer. This device comprises a pick-up to be placed on the structure surface and formed of a central cylindrical electrode, two intermediary annular electrodes and an outer annular electrode coaxial with the central electrode. A supply alternating voltage is applied between said central and outer electrodes, and the current thus produced is applied to a load resistor. The voltage across this load resistance is then measured. The inter-electrode voltage appearing between the intermediary electrodes is also measured. The component of the inter-electrode voltage cophasal with the load resistor voltage is formed and is divided by the load resistor voltage.

3 Claims, 6 Drawing Figures

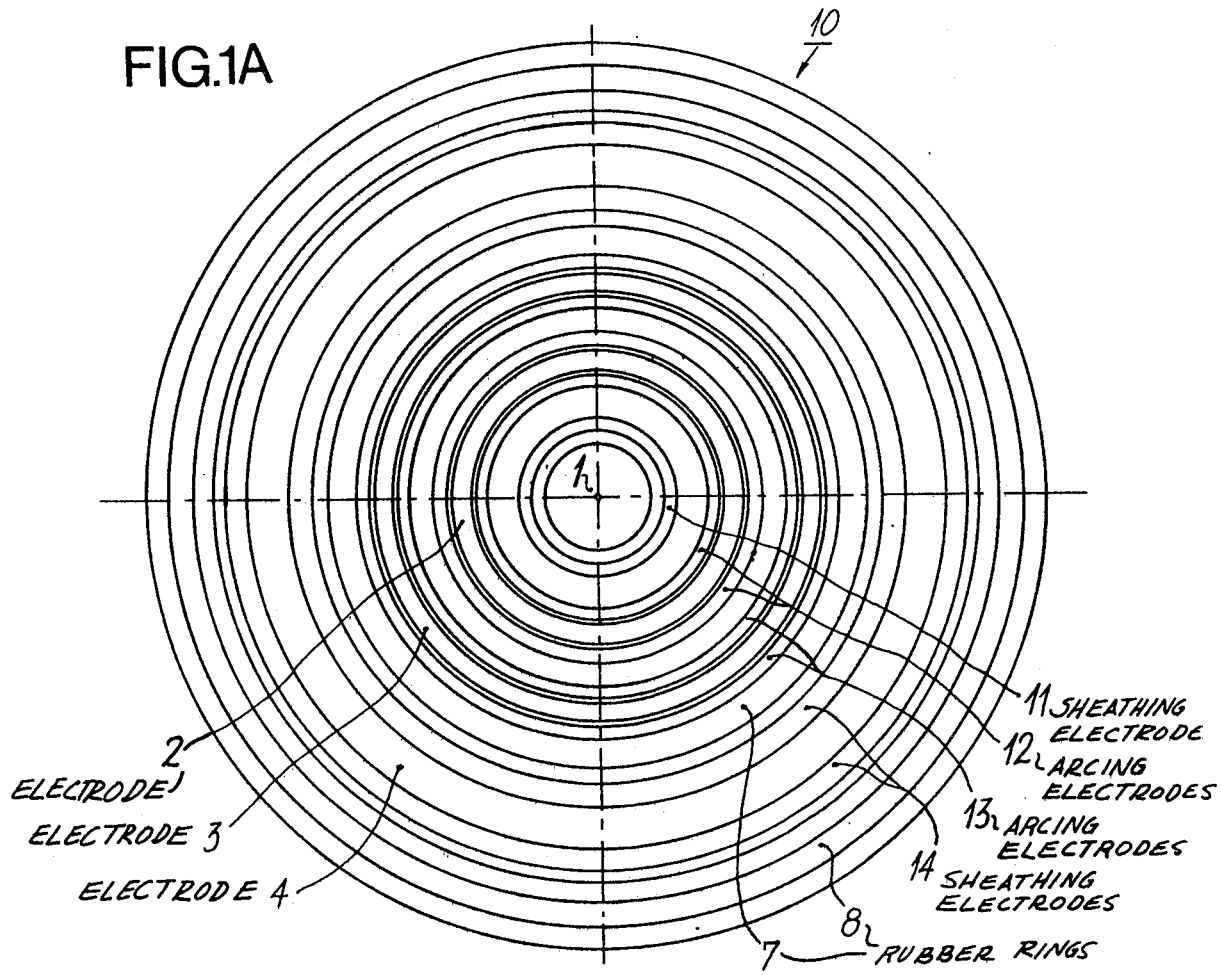
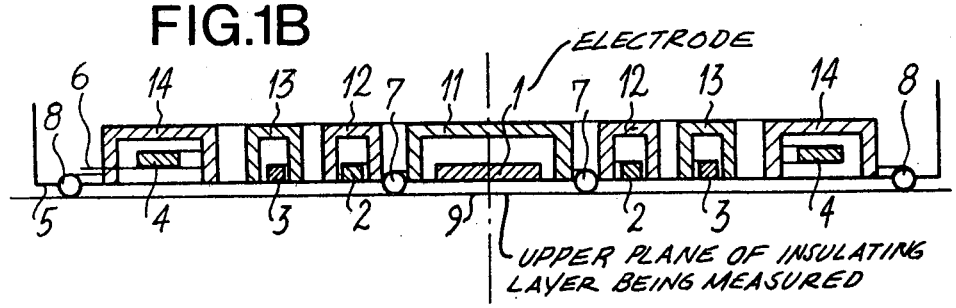

SURFACE RESISTIVIMETER

BACKGROUND OF THE INVENTION

1. Field of the Invention

The present invention concerns an antistatic surface coating checking device for ensuring that a structure having a metal frame including both metal panels and insulating panels coated with a layer of conducting material, the surface of these panels being entirely finished with an insulating paint, is capable of withstanding the action of the electrostatic phenomena to which it is subjected with no adverse effect. To be more precise, this device makes it possible to measure layer resistances in the range between $10^5$ and $10^8$ ohms per square, with a view to checking out the effectiveness of the antistatic protection provided by the conducting layers covering the structure insulating elements.

Antistatic protective measures, particularly those employed in the aerospace industry, can be broken down into two categories:

those applied to structural elements not requiring radioelectric transparency properties (example: access doors, wing sections, tip ends, etc);

those applied to the dielectric walls protecting navigation, communication or detection equipment and consequently calling for radioelectric transparency properties (example: radome, aerial fairings, missile caps, etc.).

In the first case, the antistatic deposits applied can have very low surface resistance values. In the second case, the deposits made must provide high and perfectly controlled surface resistances in order to afford a compromise between the continual flow of static charges and the necessary radio-transparency properties. This compromise gives rise, in the majority of applications, to surface resistances in the range between $10^5$ and $10^8$ ohms per square.

In virtually all aerospace applications (airplanes, helicopters, missiles), the antistatic treatments are themselves followed by the application of a finishing paint (for the purposes of aesthetics as regards commercial aircraft, optical detection for the experimental missiles, particle impact resistance, corrosion immunity, thermal balance, etc . . . ). This finishing paint is an insulator and rules out, on the face of it, any process for measuring or checking the subjacent electrostatic protection using electrodes in electrical contact (megohmmeter with plan or circular electrodes).

2. Description of the Prior Art

French Pat. No. 1 333 449 filed Sept. 12, 1962 discloses a surface resistivimeter having central and annular coaxial electrodes made of conducting rubber. This resistivimeter permits the resistances of bare metallic surfaces to be measured; it cannot measure the resistances of surfaces coated with an insulating layer.

SUMMARY OF THE INVENTION

The resistivimeter device intended for measuring the surface resistance of resistive layers coated with superficial insulating layers comprises a pick-up formed of a central cylindrical electrode, two intermediary annular electrodes coaxial with the central electrode and an outer annular electrode coaxial with the central and intermediary electrodes, means for applying an alternating voltage supply between the central and outer electrodes and means for measuring the voltage appearing between the intermediary electrodes. The invention is characterized by the fact that the intermediary electrodes are enveloped by arcing electrodes and that the device comprises unit followers bringing each arcing electrode to an instantaneous potential equal to that of the electrode it surrounds in order to reduce the capacity between adjacent intermediary electrodes to that part of this capacity exerted across the insulating layer, and means for dividing a component of the measuring voltage by a voltage proportional to the current circulating in the resistive layer where the said measuring voltage component is in phase with the proportional voltage.

BRIEF DESCRIPTION OF THE DRAWINGS

The invention is now described in detail with reference being made to the drawings attached hereto in which:

FIGS. 1A and 1B are respectively plan and side sectional views of the preferred embodiment of a resistivimeter in accordance with the invention;

DESCRIPTION OF THE PREFERRED EMBODIMENTS

Figure 2:
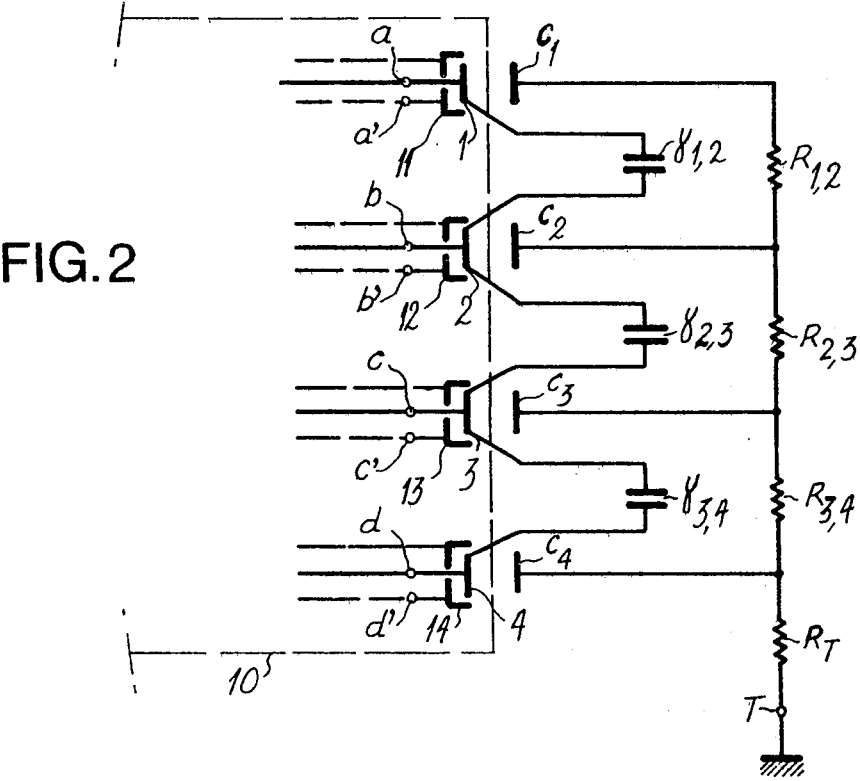
FIG. 2 is a partial electrical diagram of a pick-up having two intermediary electrodes for measuring surface resistance.

The following symbols are used hereinafter:

$R_{1,2}$, $R_{2,3}$, $R_{3,4}$ and $R_T$ are respectively the resistance values of the resistive layers between the first and second, second and third, and third and fourth electrodes, and between the latter electrode and ground;

$C_1$, $C_2$, $C_3$, $C_4$ are respectively the capacitances between the faces of the first, second, third and fourth electrodes resting on the insulating layer and the resistive layer situated beneath this insulating layer;

$\gamma_{1,2}$, $\gamma_{2,3}$, $\gamma_{3,4}$ are respectively the capacitances between the first and second, second and third, and third and fourth electrodes across the insulating layer;

$R_s$ is the surface resistance per square of the resistive layer $$R_S = \rho/e$$

where $\rho$ is the resistivity and e the thickness of the insulating layer;

i is the current flowing in the resistances $R_{1,2}$, $R_{2,3}$ and $R_{3,4}$ and the capacitances $\gamma_{1,2}$, $\gamma_{2,3}$ and $\gamma_{3,4}$;

R is the value of the load resistor across which the current is measured;

$V_{bc}$ is the voltage between the intermediary electrodes;

$V_{ef}$ is the voltage across the load resistor terminals; and $V_{bc}^{(1)}$ is the component of $V_{bc}$ in phase with $V_{ef}$.

Between resistances $R_S$ and $R_{2,3}$ the relationship is as follows:

$$R_s = \frac{2\pi R_{2,3}}{\log(r_3/r_2)} \quad (1)$$

where $r_2$ and $r_3$ are the radii of the intermediary electrodes.

The voltage across the load resistor terminals is given by:

$$V_{ef} = Ri$$

The device also measures the voltage between the two intermediary electrodes $V_{bc}$ and the component $V_{bc}^{(1)}$ thereof which is cophasal with $V_{ef}$, as a result:

$$R_{2,3}/R = V_{bc}^{(1)}/|V_{ef}| \qquad (2);$$

by replacing $R_{2,3}$ with the value therefore given by (1):

$$R_S = \frac{2\pi R}{\log(r_3/r_2)} \times V_{bc}^{(1)}/|V_{ef}|; \qquad (3)$$

The pick-up 10 intended to contact an insulating layer having an upper surface in plane 9 is shown in FIGS. 1A and 1B as comprising a central cylindrical electrode 1, and two intermediary annular electrodes 2 and 3, and an outer annular electrode 4; electrodes 2, 3 and 4 are cylindrical and coaxial with central electrode 1. Certain of the electrodes, 1 and 4 are enveloped, apart from the side thereof resting on the insulating layer, by sheathing electrodes 11 and 14 respectively set at a fixed potential. The other electrodes 2 and 3 are respectively enveloped, except on the side thereof resting on the insulating layer, by arcing electrodes 12 and 13, held at the same potential as electrodes 2 and 3 by unit followers 105 and 106, FIG. 3.

Central electrode 1, intermediary electrodes 2 and 3, the edges of sheating electrodes 11 and 14 and the edges of arcing electrodes 12 and 13 lie in a single plane 5 which is slightly pocketed with respect to plane 9 in which the pick-up rests on the insulating layer. The lower surface of outer electrode 4 lies in plane 6 slightly pocketed with respect to plane 5. Electrode 4 thus offers a lower capacitance than the other electrodes with respect to the insulating layer of plane 9 and, as a result, a higher impedance.

This reactive impedance is greater than the maximum resistance value of the resistive layer so that the current fed to the resistive layer is in quadrature with the supply voltage regardless of the resistance value to be measured in the envisioned range.

Rings 7 and 8, composed of flexible material, are partially embodied in the pick-up so the lower tangent plane 9 thereof protrudes slightly from plane 5 in such a way that the rings allow non-slip contact on the surface of the insulating paint layer.

Figure 3:
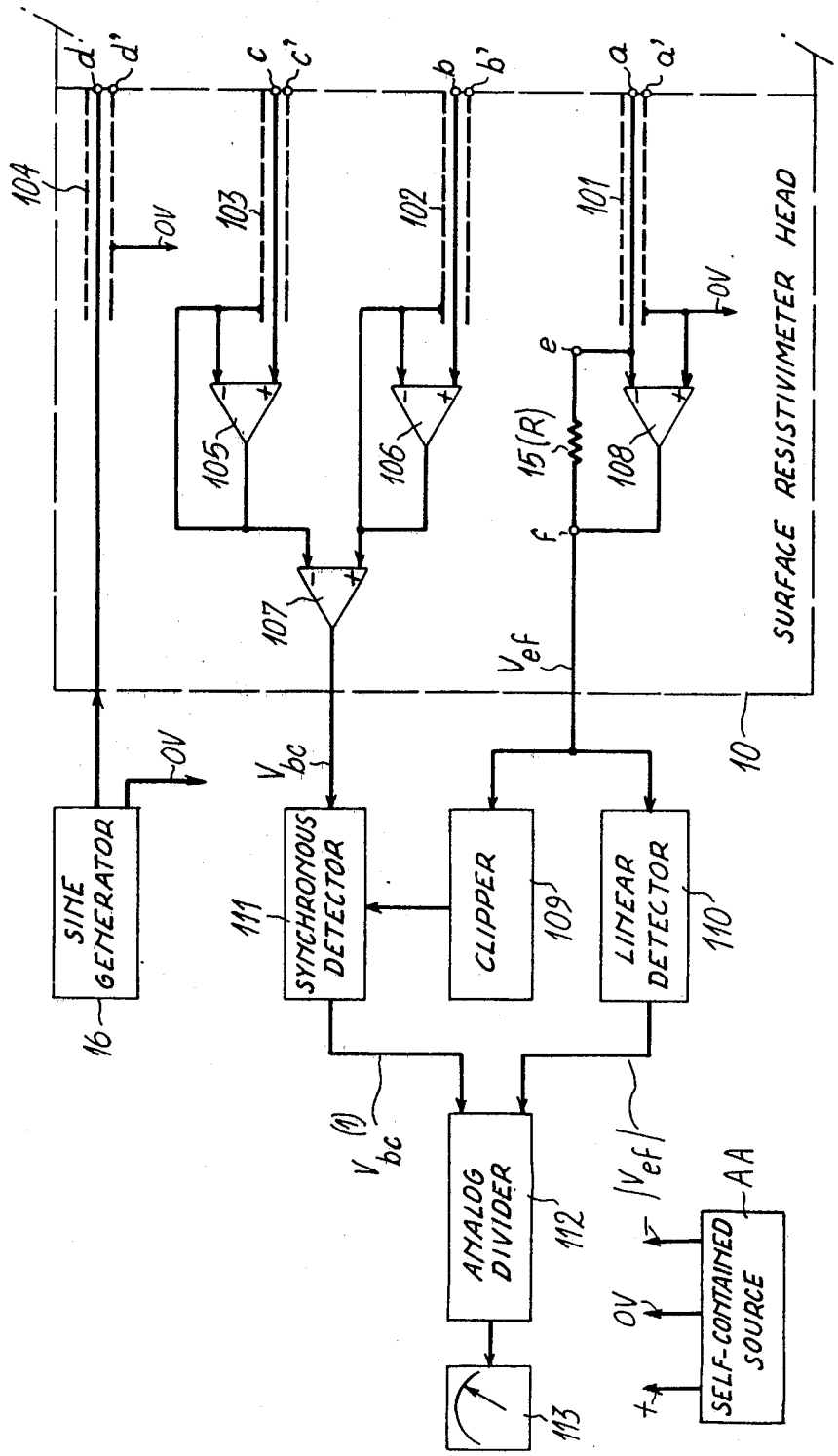
FIG. 3 is a block diagram of the electronic circuitry associated with the pick-up in FIG. 2.

Pick-up 10 further comprises several amplifiers 105, 106, 107 and 108, described in reference to FIG. 3.

With reference to FIG. 2, rectangle 10 in dotted lines represents that part of the pick-up located at the electrodes for measuring a surface resistance.

The portions of the resistive layer between electrodes 1 and 2, 2 and 3, and 3 and 4 are respectively represented by resistors $R_{1,2}$, $R_{2,3}$ and $R_{3,4}$; the portions of the insulating layer between electrodes 1, 2, 3 and 4 respectively and the resistive layer are represented by capacitors $C_1$, $C_2$, $C_3$ and $C_4$, and the capacities between electrodes across the insulating layers are represented by $\gamma_{1,2}$, $\gamma_{2,3}$ and $\gamma_{3,4}$.

Figure 5:
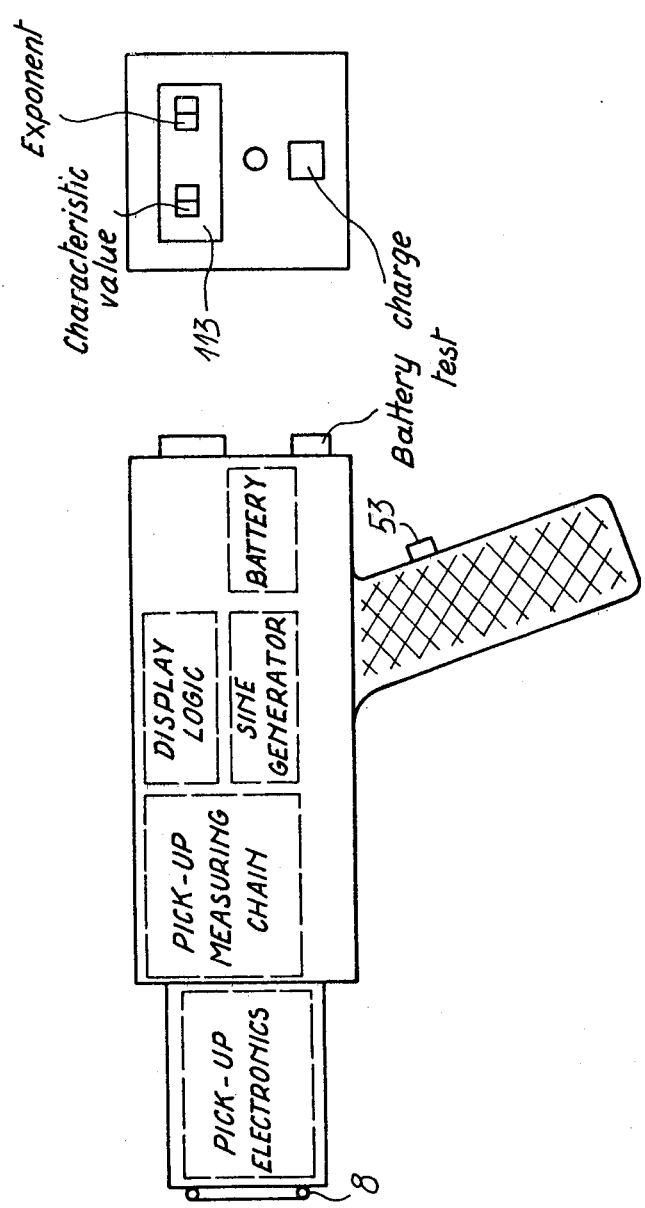
FIG. 5 is a schematic view of a second portable embodiment of the invention.

Sheating electrodes 11 and 14 are brought to a fixed potential, the reference, ground or zero potential of self-contained supply AA; arcing electrodes 12 and 13 are respectively maintained at the potentials of electrodes 2 and 3 by unit followers 105 and 106 (FIG. 5).

Alternating, sine wave generator 16 is directly connected to terminal d and the ground potential of self-contained source AA. Voltage $V_{ef}$, at the load resistor terminals, and voltage $V_{bc}$, between the intermediary electrode terminals, are processed in the FIG. 3 circuit.

FIG. 3 is a schematic electronic diagram of the resistivimeter 10, FIG. 2. As indicated on FIG. 2 terminals a, b, c and d are connected to the internal conductors of coaxial cables 101, 102, 103, 104 and terminals a', b', c' and d' are connected to the outer conductors of these coaxial cables. High frequency sinusoidal generator 16 is connected to terminal d', maintained at the grounded potential of self-contained source AA.

Signals fed to terminals b and c are applied to impedance matching, unit follower circuits 105 and 106, having unit gain and very high input impedance ($\geq 10^{10}$ Ohms). Outputs of unit followers 105 and 106 are connected to arcing electrodes 12 and 13 to raise the voltages of the electrodes permanently to the respective potentials of electrodes 2 and 3. The outputs of circuits 105 and 106 are also connected to the inputs of an operational amplifier 107.

Terminal a is connected to the input of current-voltage converter 108 that derives an output voltage $V_{ef}$, proportional to Ri, where R is the resistance value of load resistor 15. The output of converter 108 is connected to clipper circuit 109 on the one hand and linear detector 110 on the other hand. Synchronous detector 111 responds to a reference phase signal from clipper circuit 109 and the $V_{bc}$ signal to derive a $V_{bc}$ component $V_{bc}^{(1)}$ in phase with $V_{ef}$.

The outputs of linear detector 110 and synchronous detector 111 are connected to the inputs of an analog divider 112 which performs the division operation:

$$V_{bc}^{(1)}/V_{ef}$$

A measuring device 113 is connected to respond to the output of divider 112.

Figure 4:
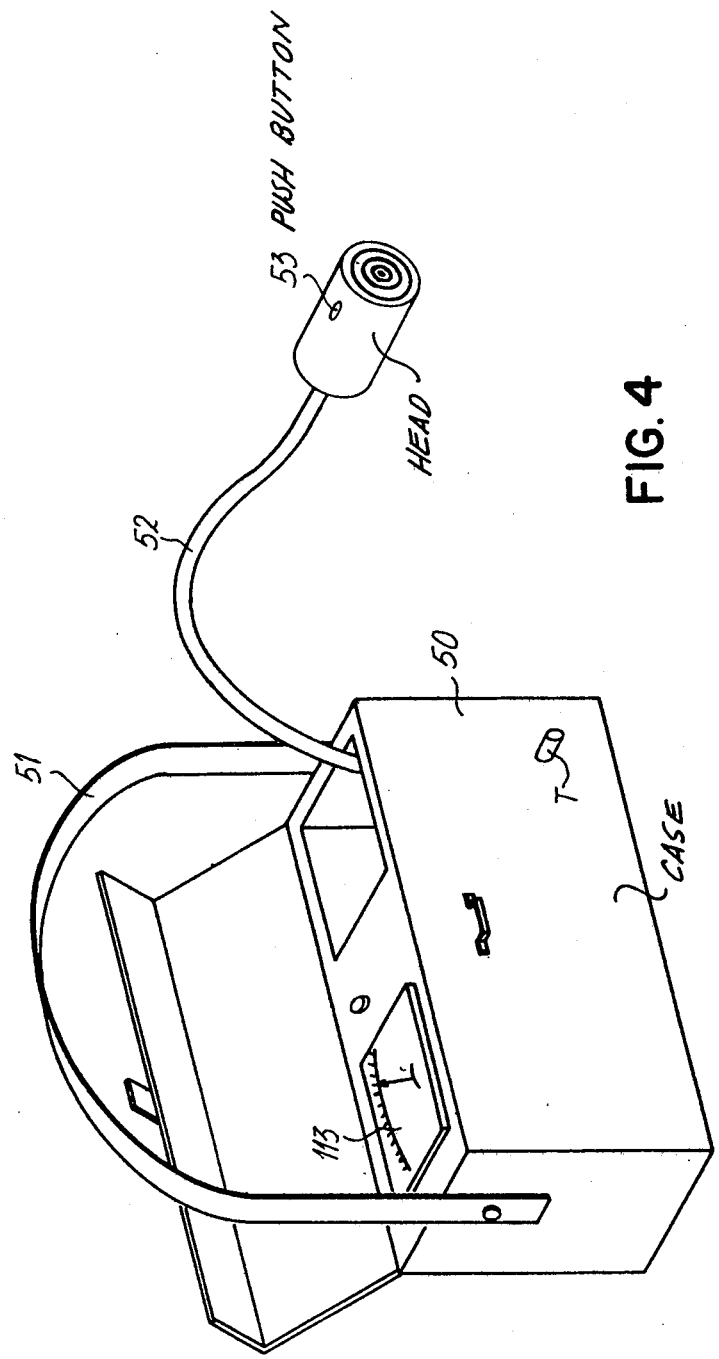
FIG. 4 is a perspective view of one portable embodiment of the invention.

FIG. 4 is a perspective view of a portable embodiment of the invention including two parts comprising a case 50 and a cylindrical head including the pick-up in FIG. 2 with electronic elements 105, 106, 107 and 108. Case 50 is fitted with a strap 51 for carrying the device around the neck and is linked by a flexible cable 52 to the pick-up. The head includes a push-button 53 for switching on equipment solely for the time required to perform an operation. The case 50 contains all the electronic assemblies shown in FIG. 3. Meter 113, providing a visual indication of the outcome of the operation, is positioned to be visible on the upper part of the case. Space is provided in the case for stowing the heads and the connection cables therefor when not in use.

FIG. 5 is a diagram of another embodiment of the invention wherein the head and processing circuits are contained in a single unit. The FIG. 5 embodiment is shaped like a piston having a barrel made up of the head in FIG. 3 which may be clipped in place. Rubber ring 8 which contacts the surface to be tested protrudes from the head of the pistol. The electronic circuit energizing push-button 53 is placed on the pistol grip. The tell-tale indicator 113 is positioned on the rear side. In this version, indicator 113 is not a needle indicator but is a digital display scientifically presenting a mantissa plus an exponent of the result.

What we claim is:

1. A resistivimeter device for measuring the surface resistance of a structure coated with an inner resistive layer and an outer insulating superficial layer, said device comprising:

a pick-up to be placed on said structure surface, formed of a central cylindrical electrode, two intermediary annular electrodes and an outer annular electrode coaxial with said central electrode;

annular arcing electrodes surrounding said intermediary electrodes except on the part thereof lying on the structure surface;

unit follower means bringing said arcing electrodes to a potential respectively equal to that of the surrounded intermediary electrodes;

annular sheathing electrodes surrounding said central and outer electrodes except on the part thereof lying on the structure surface, said sheathing electrodes being brought to a predetermined potential;

means for applying a supply alternating voltage between said central and outer electrodes, thereby producing a current between said electrodes;

means for applying said current to a load resistor and measuring the voltage across said load resistor;

means for measuring the inter-electrode voltage appearing between said intermediary electrodes;

means for forming the component of said inter-electrode voltage cophasal with said load resistor voltage; and means for dividing said component voltage by said load resistor voltage.

2. A resistivimeter device for measuring the surface resistance of a structure coated with an inner resistive layer and an outer insulating superficial layer, said device comprising:

a pick-up to be placed on said structure surface, formed of a central cylindrical electrode, two intermediary annular electrodes and an outer annular electrode coaxial with said central electrode, said central and intermediary annular electrodes having their ends located in one and the same first plane and said outer annular electrode having its end located in a second plane more distant from the structure surface than said first plane, whereby said outer annular electrode has with respect to the structure surface an impedance larger than the impedance of the central and intermediary annular electrodes with respect to said surface;

means for applying a supply alternating voltage between said central and outer electrodes, thereby producing a current between said electrodes, said current being substantially in phase quadrature with respect to said supply alternating voltage due to said larger impedance;

means for applying said current to a load resistor and measuring the voltage across said load resistor;

means for measuring the inter-electrode voltage appearing between said intermediary electrodes;

means for forming the component of said inter-electrode voltage cophasal with said load resistor voltage; and means for dividing said component voltage by said load resistor voltage.

3. A resistivimeter device for measuring the surface resistance of a structure coated with an inner resistive layer and an outer insulating superficial layer, said device comprising:

a pick-up to be placed on said structure surface, formed of a central cylindrical electrode, two intermediary annular electrodes and an outer annular coaxial with said central electrode;

arcing electrodes surrounding said intermediary electrodes except on the part thereof lying on the structure surface;

unit follower means bringing said arcing electrodes to a potential respectively equal to that of the surrounded intermediary electrodes;

annular sheathing electrodes surrounding said central and outer electrodes except on the part thereof lying on the structure surface, said sheathing electrodes being brought to a predetermined potential;

said central intermediary annular electrodes, annular arcing electrodes and annular sheathing electrodes having their ends located in one and the same first plane and said outer annular electrode having its ends located in a second plane more distant from the structure surface than said first plane, whereby said outer annular electrode has with respect to the structure surface an impedance larger than the impedance of the central, intermediary and sheathing annular electrodes with respect to the said surface;

means for applying a supply alternating voltage between said central and outer electrodes, thereby producing a current between said electrodes, said current being substantially in phase quadrature with respect to said supply alternating voltage due to said larger impedance;

means for applying said current to a load resistor and measuring the voltage across said load resistor;

means for measuring the inter-electrode voltage appearing between said intermediary electrodes;

means for forming the component of said inter-electrode voltage cophasal with said load resistor voltage; and means for dividing said component voltage by said load resistor voltage.

* * * * *